United States Patent
Eggert et al.

(10) Patent No.: US 9,707,358 B2
(45) Date of Patent: Jul. 18, 2017

(54) DISPENSE INTERFACE WITH LOCKOUT ELEMENT

(75) Inventors: Ilona Eggert, Frankfurt am Main (DE); James Alexander Davies, Warwickshire (GB); Simon Lewis Bilton, Warwickshire (GB); David Moore, Leicestershire (GB); Steven Wimpenny, Warwickshire (GB); Christopher Nigel Langley, Warwickshire (GB)

(73) Assignee: SANOFI-AVENTIC DEUTSCHLAND GMBH, Frankfurt Au Main (DE)

( * ) Notice: Subject to any disclaimer, the term of this patent is extended or adjusted under 35 U.S.C. 154(b) by 685 days.

(21) Appl. No.: 14/113,395

(22) PCT Filed: Apr. 26, 2012

(86) PCT No.: PCT/EP2012/057687
§ 371 (c)(1),
(2), (4) Date: Oct. 23, 2013

(87) PCT Pub. No.: WO2012/146674
PCT Pub. Date: Nov. 1, 2012

(65) Prior Publication Data
US 2014/0049041 A1 Feb. 20, 2014

Related U.S. Application Data

(60) Provisional application No. 61/480,063, filed on Apr. 28, 2011.

(30) Foreign Application Priority Data

Jul. 8, 2011 (EP) .................................... 11173273

(51) Int. Cl.
*A61M 5/34* (2006.01)
*A61M 5/50* (2006.01)
(Continued)

(52) U.S. Cl.
CPC .......... *A61M 5/348* (2013.01); *A61M 5/2448* (2013.01); *A61M 5/34* (2013.01);
(Continued)

(58) Field of Classification Search
CPC ................... A61M 5/50; A61M 5/502; A61M 2005/5033; A61M 5/504;
(Continued)

(56) References Cited

U.S. PATENT DOCUMENTS 5,658,257 A 8/1997 Ryles
5,984,899 A * 11/1999 D'Alessio ........... A61M 5/3271
604/192

(Continued)

FOREIGN PATENT DOCUMENTS

| | | |
|---|---|---|
| JP | 2008-212645 | 9/2008 |
| WO | 2010/147552 | 12/2010 |
| WO | WO 2010147552 A1 * | 12/2010 ............ A61M 5/326 |

OTHER PUBLICATIONS

International Search Report for Int. App. No. PCT/EP2012/057687, completed Aug. 13, 2012.

*Primary Examiner* — Bhisma Mehta
*Assistant Examiner* — William Frehe
(74) *Attorney, Agent, or Firm* — McDonnell Boehnen Hulbert & Berghoff LLP

(57) ABSTRACT

The invention relates to a dispense interface for use with a drug delivery device with an inner body and with a lockout element, wherein the lockout element is coupled to the inner body, wherein the lockout element is movable from a receptive condition to a locked condition, wherein in the receptive condition the dispense interface is attachable to the drug delivery device, wherein in the locked condition the dispense interface is not-attachable to the drug delivery device and wherein the lockout element is configured to
(Continued)

move from the receptive condition to the locked condition when said dispense interface is attached to and detached from said drug delivery device. The invention solves the technical problem of reducing the risk of reuse of a dispense interface, after it has already been used with a drug delivery device.

13 Claims, 14 Drawing Sheets

(51) Int. Cl.
  *A61M 5/24* (2006.01)
  *A61M 5/19* (2006.01)
  *A61M 5/20* (2006.01)
  *A61M 5/31* (2006.01)
(52) U.S. Cl.
  CPC .............. *A61M 5/345* (2013.01); *A61M 5/50* (2013.01); *A61M 5/19* (2013.01); *A61M 5/2066* (2013.01); *A61M 2005/2414* (2013.01); *A61M 2005/3125* (2013.01); *A61M 2005/3128* (2013.01); *A61M 2205/502* (2013.01); *F04C 2270/0421* (2013.01)
(58) Field of Classification Search
  CPC .... A61M 2005/5046; A61M 2005/506; A61M 5/5066; A61M 5/3272; A61M 2005/3206; A61M 2005/3226; A61M 2005/3253; A61M 25/0014; A61M 2005/325; A61M 5/3269; A61M 5/3271
  See application file for complete search history.

(56) References Cited

U.S. PATENT DOCUMENTS

2005/0236787 A1* 10/2005 Weber ...................... B62B 1/10
                                                            280/47.35
2008/0154192 A1    6/2008 Schraga

* cited by examiner

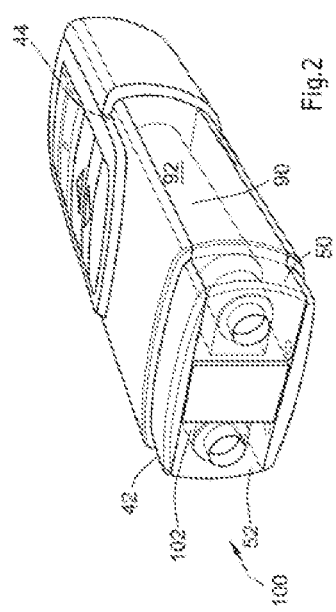
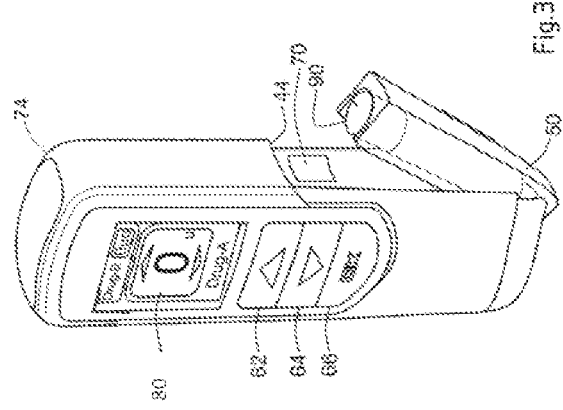

DISPENSE INTERFACE WITH LOCKOUT ELEMENT

CROSS REFERENCE TO RELATED APPLICATIONS

The present application is a U.S. National Phase Application pursuant to 35 U.S.C. §371 of International Application No. PCT/EP2012/057687 filed Apr. 26, 2012, which claims priority to U.S. Provisional Patent Application No. 61/480,063 filed Apr. 28, 2011, and European Patent Application No. 11173273.1 filed Jul. 8, 2011. The entire disclosure contents of these applications are herewith incorporated by reference into the present application.

FIELD OF DISCLOSURE

The present patent application relates to medical devices for delivering at least two drug agents from separate reservoirs. Such drug agents may comprise a first and a second medicament. The medical device includes a dose setting mechanism for delivering the drug agents automatically or manually by the user.

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

BACKGROUND

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

SUMMARY

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

Delivering one or more medicaments through a dose dispenser with a dispense interface will result in the contamination of the dispense interface with traces of each medicament. This contamination prohibits reusing the dispense interface, for example after a certain time or after a predetermined number of usages, because the purity of the delivered medicaments cannot be guaranteed. Even a user who is conscious of this problem may inadvertently try to reuse a dispense interface because he may not remember and may find it difficult or impossible to determine by inspection whether a given dispense interface has in fact been used or not.

It is therefore desirable to provide the dispense interface with a mechanism that prevents reuse of the dispense interface with a drug delivery device. This mechanism should be such that it is effective in its prevention of reuse as well as safe from manual manipulation by a user.

The invention faces the technical problem of providing a dispense interface for use with a drug delivery device which is prevented of being reused after it has already been used with a drug delivery device.

This object has been solved by a dispense interface for use with a drug delivery device with an inner body and with a lockout element, wherein the lockout element is coupled to the inner body, wherein the lockout element is movable from a receptive condition to a locked condition, wherein in the receptive condition the dispense interface is attachable to the drug delivery device, wherein in the locked condition the dispense interface is not-attachable to the drug delivery device and wherein the lockout element is configured to move from the receptive condition to the locked condition when said dispense interface is attached to and detached from said drug delivery device.

The lockout element is arranged in its receptive condition such that it allows attachment of the dispense interface to the drug delivery device. However, the process of attaching the dispense interface to the drug delivery device mechanically moves the lockout element such that, once the dispense interface is detached and thereby is removed from the drug delivery device, the lockout element mechanically blocks a reattachment of the dispense interface to any drug delivery device. Therefore a reuse of the dispense interface is prevented and the risk of contamination from residual drug components within the dispense interface eliminated.

According to an advantageous embodiment of the dispense interface, the lockout element is movable from the receptive condition to an activated condition, wherein in the activated condition the lockout element is configured to move automatically to the locked condition when said dispense interface is detached from said drug delivery device, and wherein the lockout element is configured to move from the receptive condition to the activated condition when said dispense interface is attached to said drug delivery device. This embodiment ensures in a particular safe and reliable manner the lockout element to move from the receptive condition to the locked condition, when said dispense interface is attached to and detached from said drug delivery device.

Preferably, the lockout element has at least a spring element, which in the receptive condition is strained in a first direction and in the activated and/or locked condition at least partly relaxed in a second direction, wherein the second direction is opposite to the first direction. Accordingly, when the spring element is partly relaxed in the second direction, it is less strained in the first direction. When the spring element is completely relaxed in the second direction, it is not strained in the first direction at all. Thus, the relaxing condition in the second direction directly correlates to the straining condition in the first direction.

Accordingly, in the receptive and/or the activated condition the spring element stores energy, wherein in the locked condition the spring element stores less or no energy. In this configuration, the energy in the spring element is in a simple manner transformable into movement of the lockout element, especially an automatic movement to the locked condition.

Moreover, it is preferred that the spring element in the activated condition is partly relaxed in the second direction and in the locked condition further relaxed in the second direction. Further relaxed in this context means that the spring, starting from a condition in which it partly relaxed, is moved into a condition, in which it is even more relaxed than in the prior partly relaxed condition. In particular, the spring element may thereby effect an automatic movement of the lockout element from the activated to the locked condition.

According to a further embodiment, the spring element in the activated condition is strained in a third direction and in the receptive and/or locked condition at least partly relaxed in a fourth direction, wherein the fourth direction is opposite to the third direction.

Thus, by moving the lockout element from the receptive to the activated condition, the spring element is partly relaxed in the second direction and at the same time strained in the third direction. By moving the lockout element from the activated to the locked condition, the spring element is further relaxed in the second direction and also relaxed in the fourth direction. Accordingly, the spring element in the activated condition stores energy for movement in two directions. Thereby a reliable automatic movement of the lockout element from the activated to the locked condition may be provided.

Furthermore, the spring element is preferably a combined spiral and coil spring, wherein the combined spiral and coil spring in the first direction is strained by moving its ends opposite to each other around a spiral axis, and wherein the combined spiral and coil spring in the third direction is strained by compression along the spiral axis. A combined spiral and coil spring may on the one hand be manufactured simply and therefore cost-effectively. At the same time a combined spiral and coil spring may provide resilient spring forces in more than one effective direction in a specifically simple and reliable manner.

Preferably, the combined spiral and coil spring has a conical shape, which ensures that the spring element may be compressed along its spiral axis about a large spring travel. Particularly, a combined spiral and coil spring with a conical shape may be compressed along the spiral axis up to the thickness of the spring wire.

According to yet another embodiment, the spring element comprises a first shaped element at a first end and a second shaped element at a second end. Each of the shaped elements may be provided as a spring wire portion, which is bent in a direction facing the spiral axis or facing away from the spiral axis. Shaped elements at the ends of the spring element allow the spring element to be arranged in the inner body with positive fit in a specifically simple manner. Likewise the shaped elements allow the spring element to be strained and to transfer spring forces into movement in a simple and secure manner.

A secure connection of the lockout element to the inner body may be ensured, when the inner body comprises a retaining element, in which the first shaped element of the spring element is seated with positive fit. The attachment of the lockout element to the inner body may thereby be safely maintained particularly in the locked condition. This prevents an inadvertent removal of the lockout element from the inner body and accordingly further reduces the risk of reattachment of the dispense interface after it has been used.

Furthermore, a secure movement of the second shaped element relative to the first shaped element may be realized, thus enabling reliable straining and relaxing processes of the spring element.

According to another advantageous embodiment, the inner body has a guiding track, and the second shaped element of the spring element is movably guided in the guiding track, wherein the guiding track has a receptive section, an activation section and a blocking section, wherein in the receptive condition the second shaped element is arranged in the receptive section, wherein in the activated condition the second shaped element is arranged in the activation section, and wherein in the locked condition the second shaped element is arranged in the blocking section.

Thus, the guiding track of the inner body defines sections, which correspond to the respective condition of the lockout element. By moving the second shaped element along the guiding track, the condition of the lockout element may be changed. Particularly, the straining condition may be changed, since the first shaped element may be seated with positive fit in the retaining element of the inner body and the second shaped element is hence moved relative to the first shaped element. Since the guiding track with its receptive, activation and blocking section securely guides the second shaped element, any condition change of the lockout element may be conducted reliably.

In a preferred embodiment, the second shaped element, while arranged in the receptive section, is movable in the third direction into the activation section, the second shaped element, while arranged in the activation section, is movable in the fourth direction into the blocking section, and the second shaped element, while arranged in the blocking section, is blocked in the third direction.

Thus, the second shaped element, while arranged in the receptive condition, may not be moved in the first, second and fourth direction due to geometrical restrictions.

While arranged in the activation section, the second shaped element is prevented from being moved in the second direction due to geometrical restrictions. However, the second shaped element, while arranged in the activation section, is not necessarily geometrically restricted in the first direction. Furthermore the second shaped element, while arranged in the activation section, may be movable in the third and fourth direction between a distal stop position, which is distant to the blocking section, and a proximal stop position, which is proximal to the blocking section. Thereby, in the distal stop position the second shaped element may be geometrically restricted from being further moved in the third direction, and in the proximal stop position the second shaped element may be geometrically restricted from being further moved in the fourth direction. Finally, in the proximal stop position the second shaped element is not restricted in the second direction and may preferably be geometrically restricted in the first direction.

Also, the second shaped element, while arranged in the blocking section, may be prevented from being moved in the second direction due to geometrical restrictions, and is not necessarily geometrically restricted in the first direction. As mentioned above, the second shaped element, while arranged in the blocking section, is blocked in the third direction. This blocking in the third direction is likewise realized by geometrical restrictions provided by the guiding track. However, the blocking of the second shaped element in the blocking section does not necessarily prevent any movement. Rather, the second shaped element, while arranged in the blocking section, may be movable up to a comparably short distance in the third and fourth direction. In particular, the second shaped element, while arranged in the blocking section, may be moved between a stop position in the fourth direction, in which the second shaped element is geometrically restricted from being further moved in the fourth direction, and a stop position in the third direction, in which the second shaped element may be geometrically restricted from being further moved in the third direction. These two stop positions have thus a comparably short distance to each other, such that only movement up to a short distance in the third and/or fourth direction is possible. Also, the second shaped element, while arranged in the stop position in the third direction, may be geometrically restricted in the first direction.

By providing a guiding track with the above mentioned geometrical restrictions the risk of misuse of the lockout element is reduced, whereby a reattachment of the dispense interface to a drug delivery device after it has been used may be securely prevented.

The guiding track furthermore may have a first transition section between the receptive and the activation section and a second transition section between the activation and the blocking section. Thus moving the second shaped element from the receptive to the activation section or from the activation to the blocking section, it may pass the respective transition sections. Thereby, the spring element may be enabled to relax in the respective direction in a reliable manner.

According to yet another preferred embodiment, the second shaped element, while arranged in the receptive section, is pressed in the second direction against a first support portion of the guiding track by an elastic spring force applied by the spring element, the second shaped element, while arranged in the activation section, is pressed in the second direction against a second support portion of the guiding track by an elastic spring force applied by the spring element, the second shaped element, while arranged in the blocking section, is pressed in the second direction against a third support portion of the guiding track by an elastic spring force applied by the spring element, wherein the third support portion is positioned relative to the second support portion in the second direction, and wherein the second support portion is positioned relative to the first support portion in the second direction.

Hence, the shaped element, while arranged in the receptive, the activation as well as the blocking section is pressed in the second direction against a respective support portion by an elastic spring force applied by the spring element.

Accordingly, the spring element is permanently strained in the first direction, even though the straining condition of the spring element in the first direction is changed by moving the second shaped element from the receptive to the activation section and from the activation to the blocking section, due to the fact that the second support portion is positioned relative to the first support portion in the second direction, and the third support portion is positioned relative to the second support portion in the second direction. Thereby it is ensured, that the second shaped element is not unintentionally moved in the first direction, in case no geometrical restriction in the first direction is provided in the respective position of the second shaped element. The risk of moving the second shaped element from the blocking section back to the activation section or even back to the receptive section is thus eliminated.

Moreover, the second shaped element, while arranged in the receptive and the blocking section, may be pressed in the fourth direction against a fourth and respectively a fifth support portion of the guiding track by an elastic spring force applied by the spring element. The fourth and fifth support portions may be positioned with no or only a small distance to each other in the third or fourth direction. Likewise the second shaped element, while arranged in the activation section, may be pressed in the fourth direction against a distal portion of the drug delivery device.

Accordingly, the spring element may be permanently strained in the third direction, even though the straining condition of the spring element in the third direction is changed by moving the second shaped element from the receptive to the activation section and from the activation to the blocking section. This is due to the fact, that the spring element in the activated condition is strained in a third direction and in the receptive and/or locked condition at least partly relaxed in a fourth direction.

By this arrangement it is ensured, that the second shaped element is not unintentionally moved in the third direction, in case no geometrical restrictions in the third direction is provided in the respective position of the second shaped element. In particular, the risk of unintentionally moving the second shaped element from the receptive section to the activation section or even into the blocking section is thus eliminated.

It is especially preferred, that the spring element and the guiding track are configured such that when said dispense interface is attached to said drug delivery device, a distal portion of the drug delivery device acts on the spring element, such that said spring element is strained in the third direction and the second shaped element is moved from the receptive section into the activation section, such that said spring element is partly relaxed in the second direction.

Accordingly, by attaching the dispense interface to the drug delivery device, the spring element is compressed along its spiral axis and at the same time relaxed by unwinding around its spiral axis. Therefore, energy stored in the spring element by straining it the first direction is reduced by the unwinding process around the spiral axis. This energy may reliably be transferred into an automatic movement of the lockout element from the receptive to the activated condition.

Furthermore, energy of the spring element is increased by straining the spring element in the third direction, whereby a subsequent automatic movement of the lockout element to the locked condition may be ensured.

Moreover it is preferred, that the spring element and the guiding track are configured such that when said dispense interface is detached from said drug delivery device, a distal portion of the drug delivery device is retracted from said spring element such that said spring element is at least partly relaxed in the fourth direction and the second shaped element moves automatically from the activation section into the blocking section such that said spring element is further relaxed in the second direction.

Accordingly, by detaching the dispense interface from the drug delivery device, the spring element is relaxed along its spiral axis and at the same time relaxed by unwinding around its spiral axis. Thus, the energy stored in the spring element in the activated condition by compression along the spiral axis as well as torsion around the spiral axis is reduced. This energy may reliably be transferred into an automatic movement of the lockout element from the activated to the locked condition. At the same time the detachment of the dispense interface may be supported by the relaxing process of the spring element along its spiral axis.

Furthermore, the spring element may be an integral part of the lockout element or a separate element, which is connected to the lockout element. Preferably the lockout element comprises two separate spring elements. Each spring element may be arranged at a position in the dispense interface, which corresponds to one of the drug cartridges in the drug delivery device. Thereby the reliability of the lockout element may be increased.

The dispense interface may particularly be produced cost effectively, in case each spring element is formed as one piece. Preferably the spring elements may be formed from metal, particularly from a spring wire material. Likewise the spring elements may be formed from a suitable plastic material.

According to yet another embodiment, the lockout element may have a cover plate for bearing a distal portion of the drug delivery device, wherein the cover plate is supported on the spring element. Particularly, the cover plate is supported on the spring element in the third direction.

Respectively, the cover plate may be supported on two spring elements at the same time, in case the lockout element comprises two spring elements. Likewise, the lockout element may have two separate cover plates, wherein each of the cover plates is supported on one of the spring elements.

Thus, by attaching the dispense interface to a drug delivery device, a distal end of the drug delivery device acts on the cover plate and therefore indirectly on the spring element or the spring elements. The risk of jamming of the spring element may thereby be reduced.

The dispense interface is preferably configured to be used with a drug delivery device, in particular with a drug delivery device mentioned at the beginning, whereby the dispense interface is removably attached to the drug delivery device. By detaching the dispense interface from the drug delivery device, it may, due to the lockout element moving to the locked condition, not be reattached to the drug delivery device. The risk of contamination from residual drug components within the dispense interface is thus eliminated.

BRIEF DESCRIPTION OF THE FIGURES

These as well as other advantages of various aspects of the present invention will become apparent to those of ordinary skill in the art by reading the following detailed description, with appropriate reference to the accompanying drawings, in which:

FIG. 2 illustrates a perspective view of the delivery device distal end showing the cartridge;

FIG. 3 illustrates a perspective view of the delivery device illustrated in FIG. 1 or 2 with one cartridge retainer in an open position;

DETAILED DESCRIPTION

Figure 1:
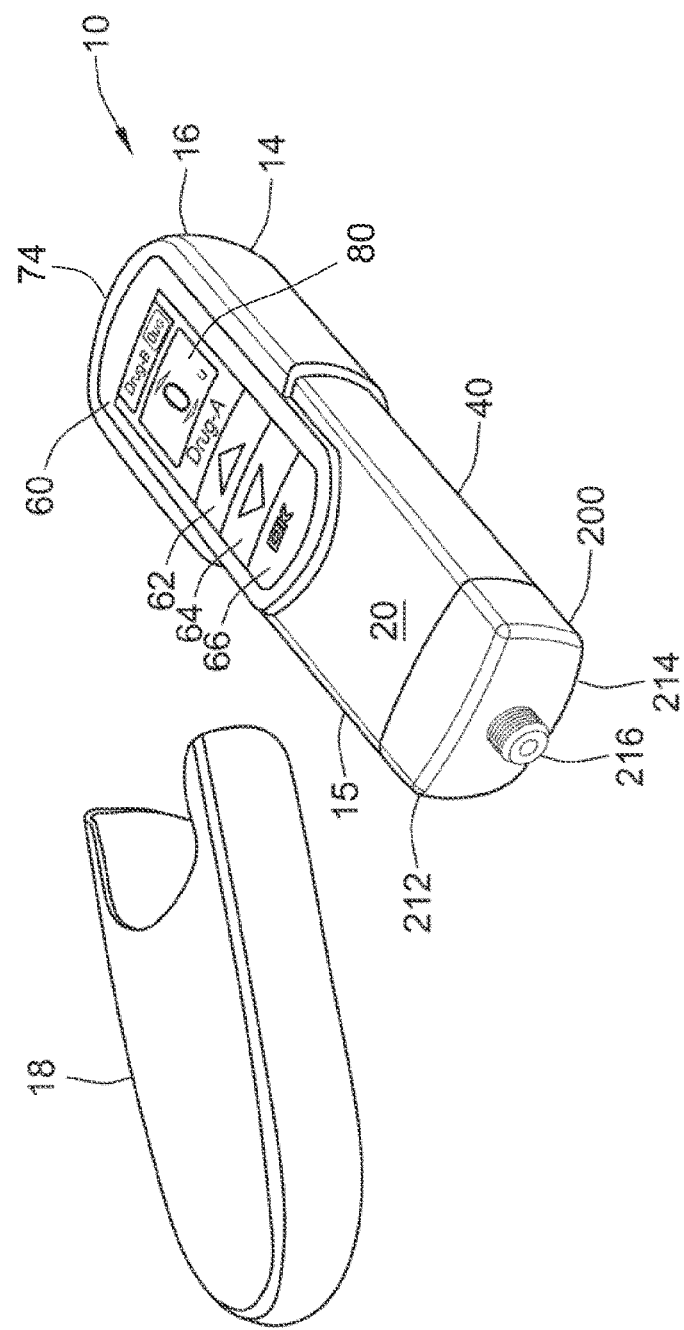
FIG. 1 illustrates a perspective view of a delivery device with an end cap of the device removed.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body 14, an injection button 74 is also provided (not visible in the perspective view of FIG. 1).

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information 84, preferably information relating to the medicaments contained within the cartridge holder 40. For example, the user is provided with certain information relating to both the primary medicament (Drug A) and the secondary medicament (Drug B).

As shown in FIG. 3, the first and second cartridge retainers 50, 52 may be hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
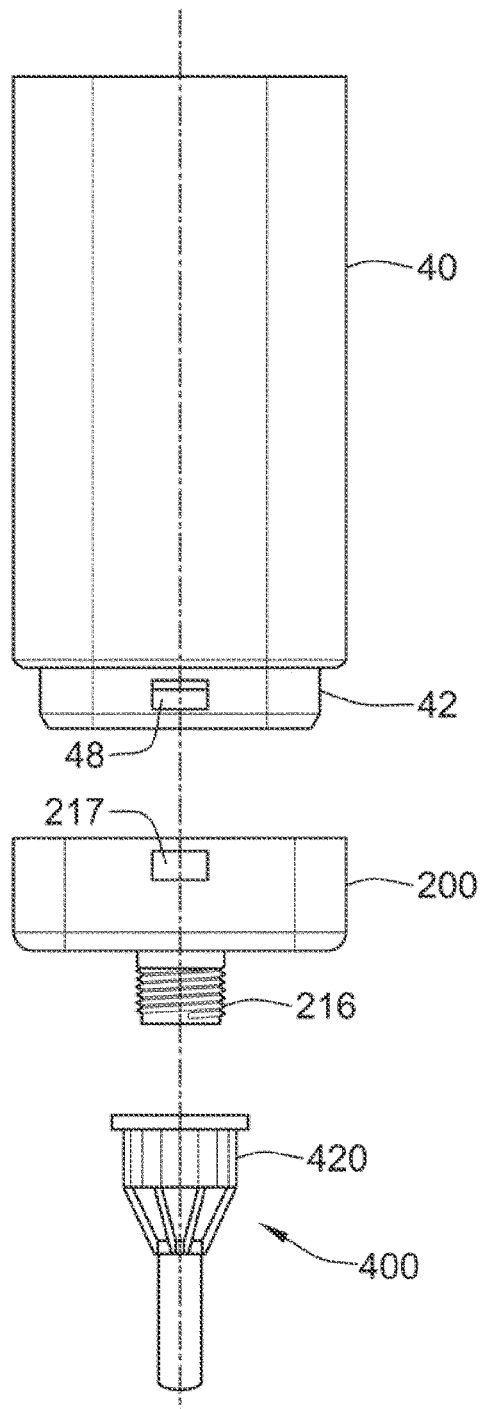
FIG. 4 illustrates a dispense interface and a dose dispenser that may be removably mounted on a distal end of the delivery device illustrated in FIG. 1.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly that may be used with the interface 200 is also illustrated and is provided in a protective outer cap 420.

Figure 5:
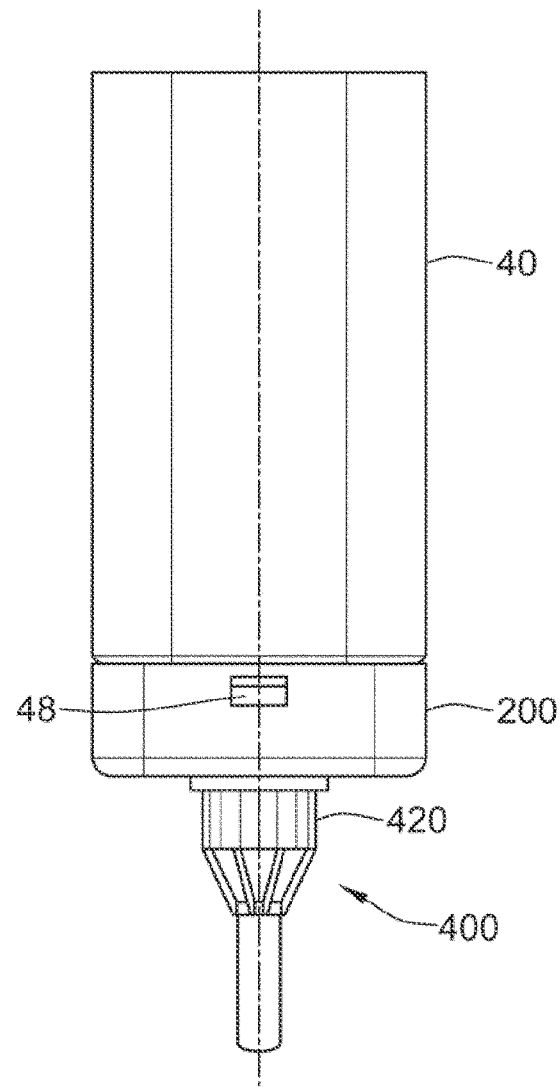
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
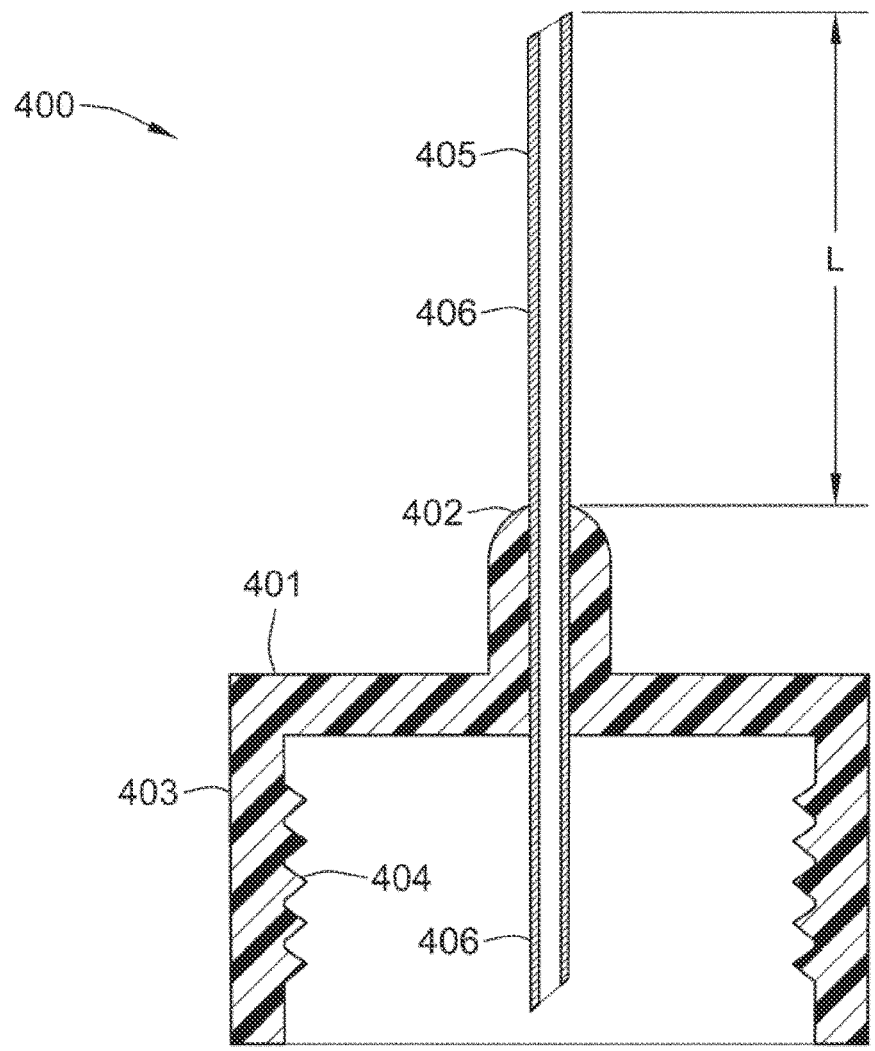
FIG. 6 illustrates one arrangement of a needle assembly that may be mounted on a distal end of the delivery device.
Figure 7:
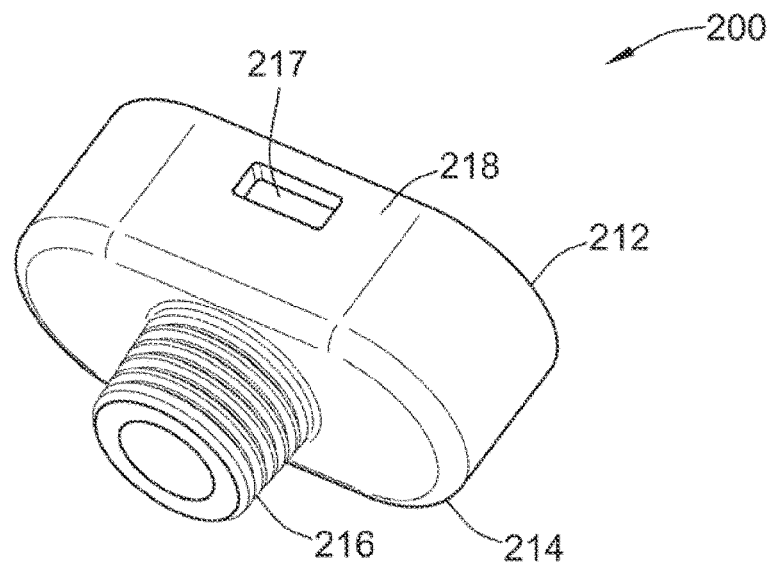
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 402 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 406 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:
  a. a main outer body 210,
  b. an first inner body 220,
  c. a second inner body 230,
  d. a first piercing needle 240,
  e. a second piercing needle 250,
  f. a valve seal 260, and
  g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213*a* and a second rib 213*b*. This first rib 213*a* is also illustrated in FIG. 10. These ribs 213*a* and 213*b* are positioned along the inner surface 215 of the wall 218 of the outer body 210 and create a form fit or snap lock engagement with cooperating grooves 224*a* and 224*b* of the first inner body 220. In a preferred arrangement, these cooperating grooves 224*a* and 224*b* are provided along an outer surface 222 of the first inner body 220.

Figure 8:
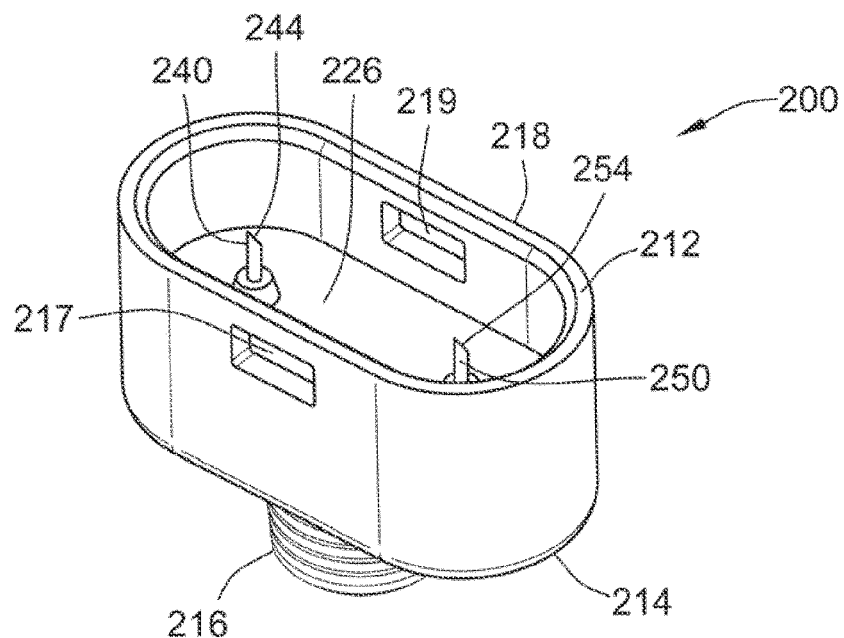
FIG. 8 illustrates another perspective view of the dispense interface illustrated in FIG. 4.
Figure 9:
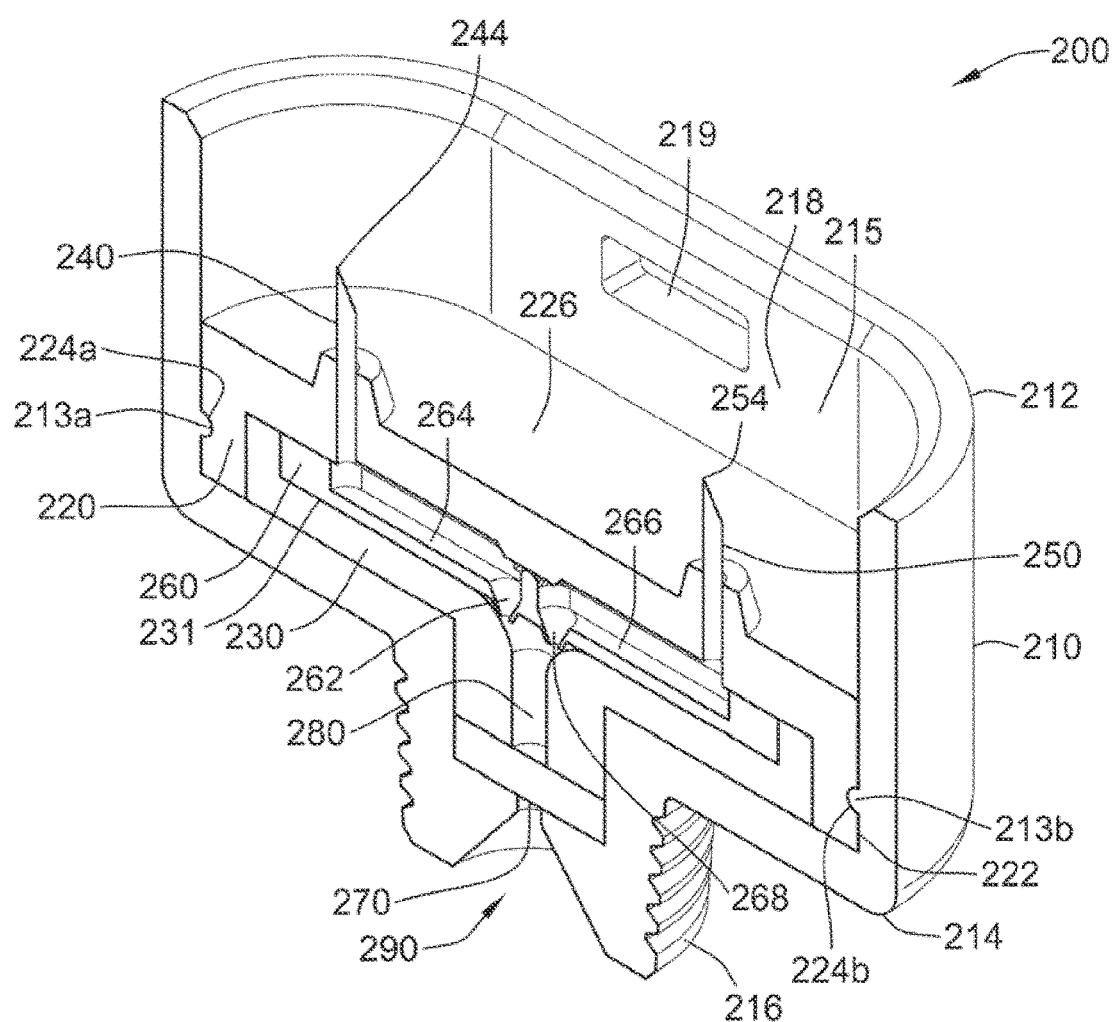
FIG. 9 illustrates a cross-sectional view of the dispense interface illustrated in FIG. 4.
Figure 10:
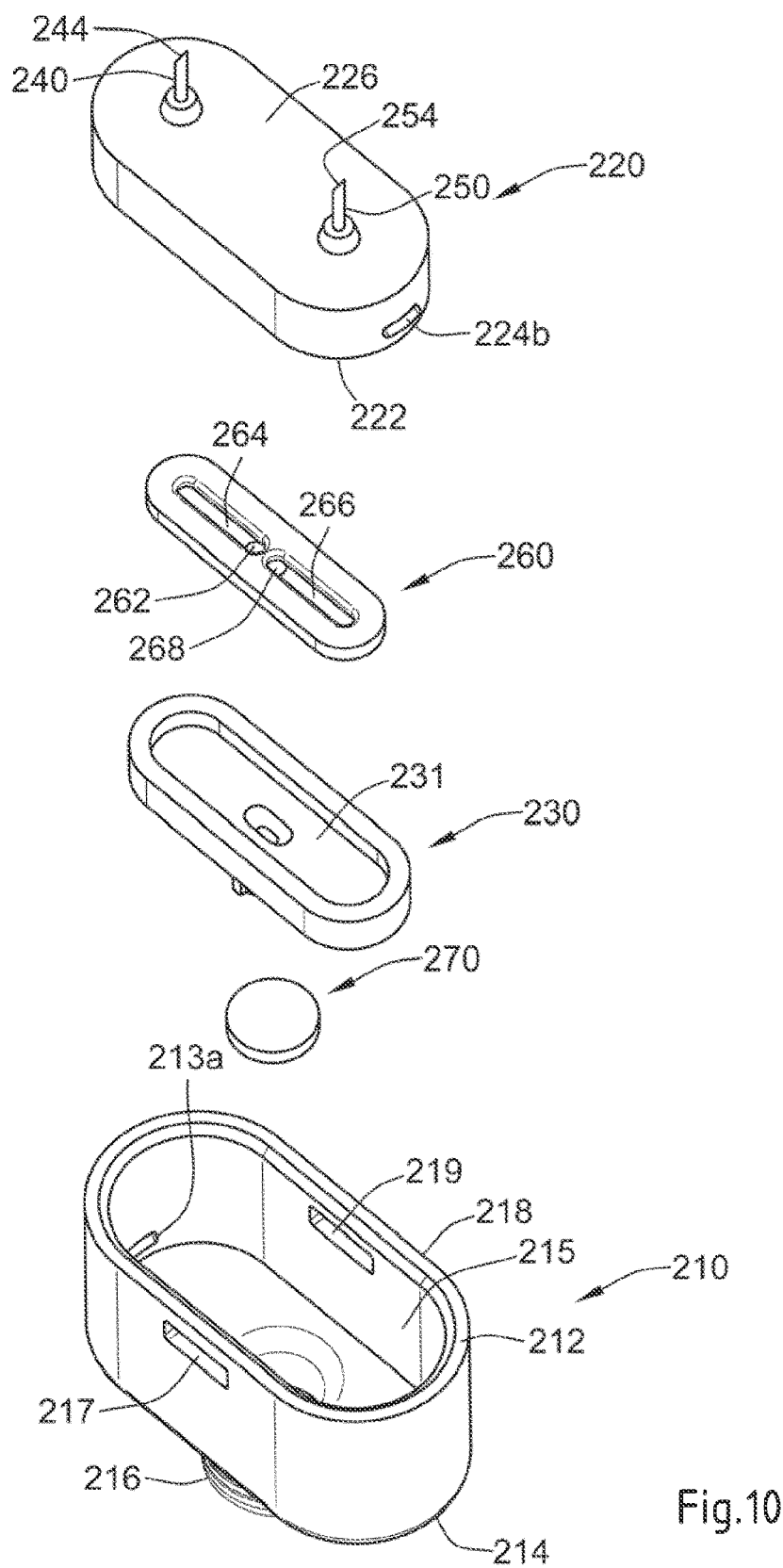
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
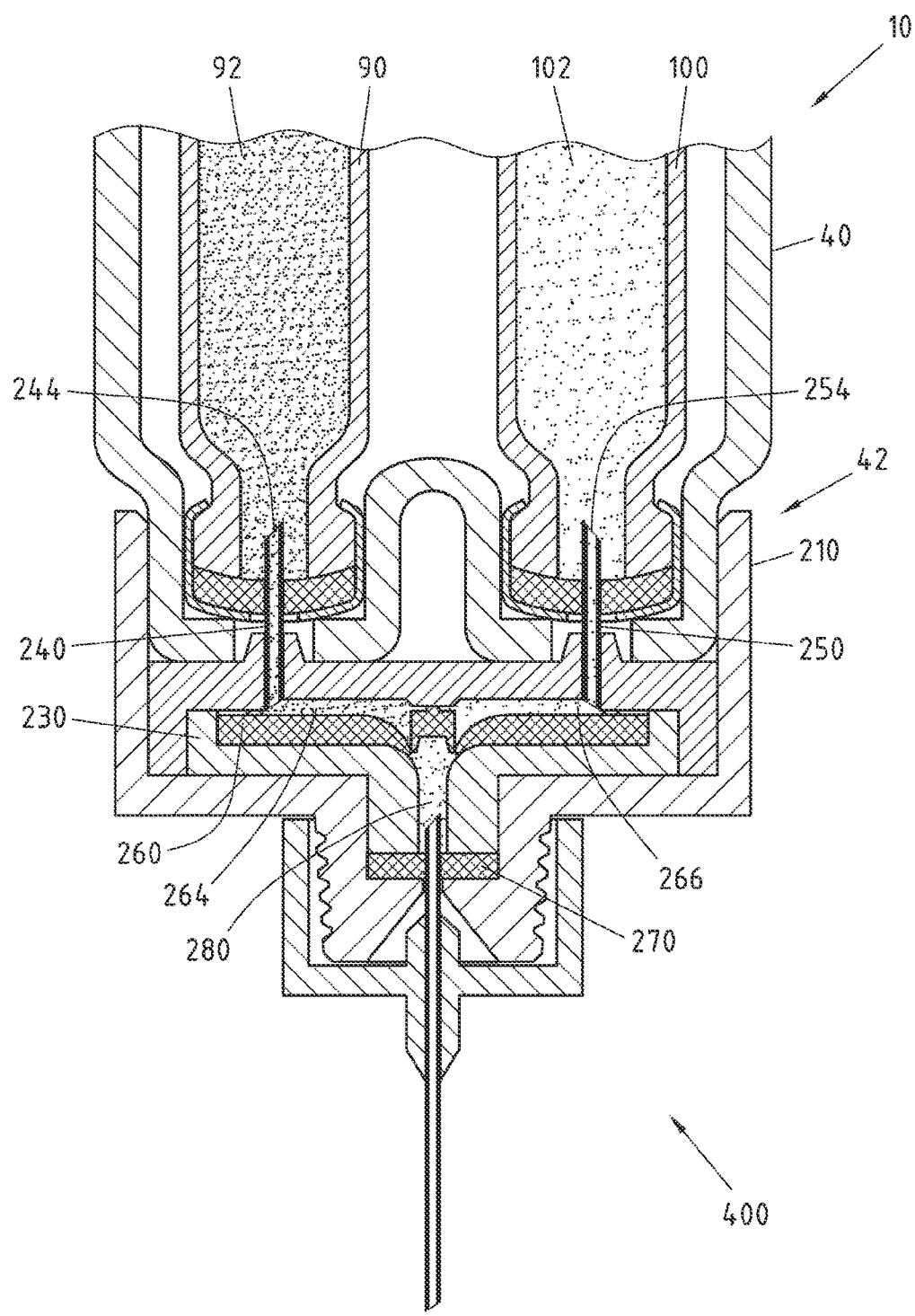
FIG. 11 illustrates a cross-sectional view of the dispense interface and needle assembly mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

Embodiments of a dispense interface with a lockout element and an inner body will be described in detail hereinafter.

Figure 12:
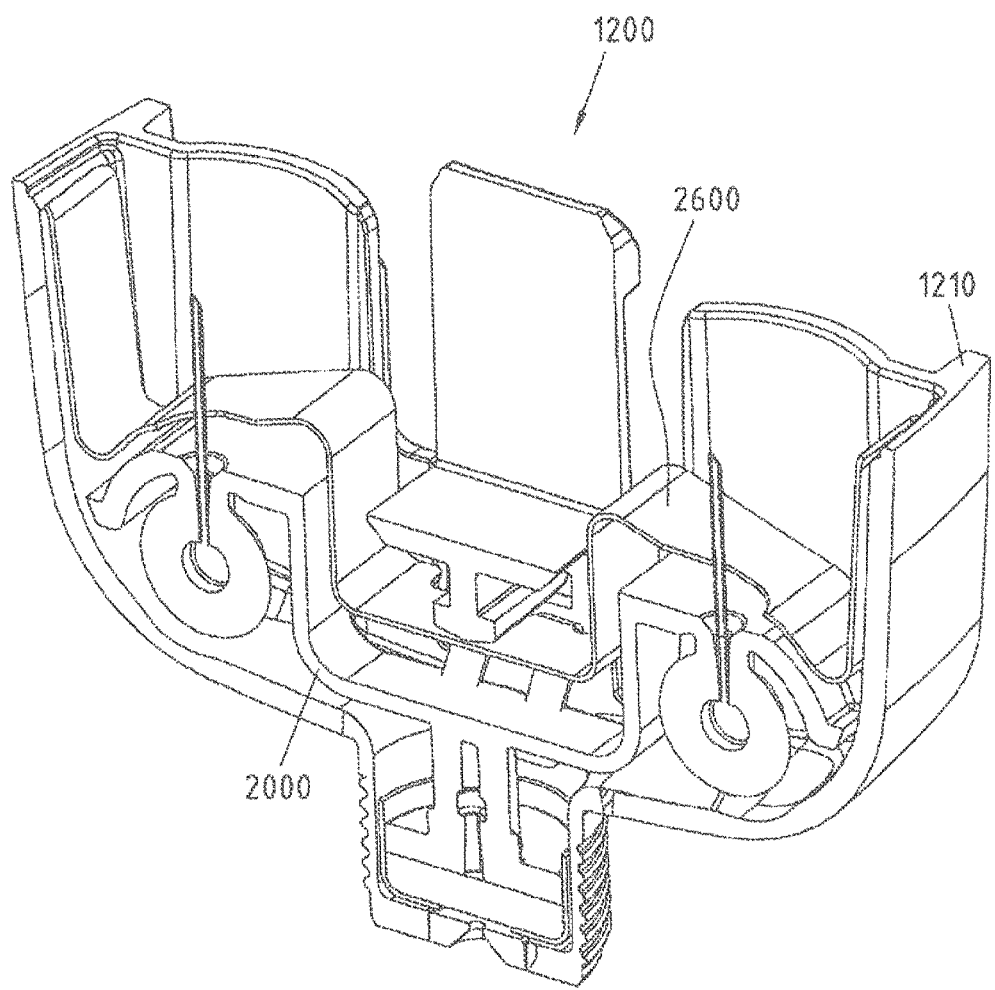
FIG. 12 illustrates a perspective view of the dispense interface with an inner body and a lockout element.
Figure 13:
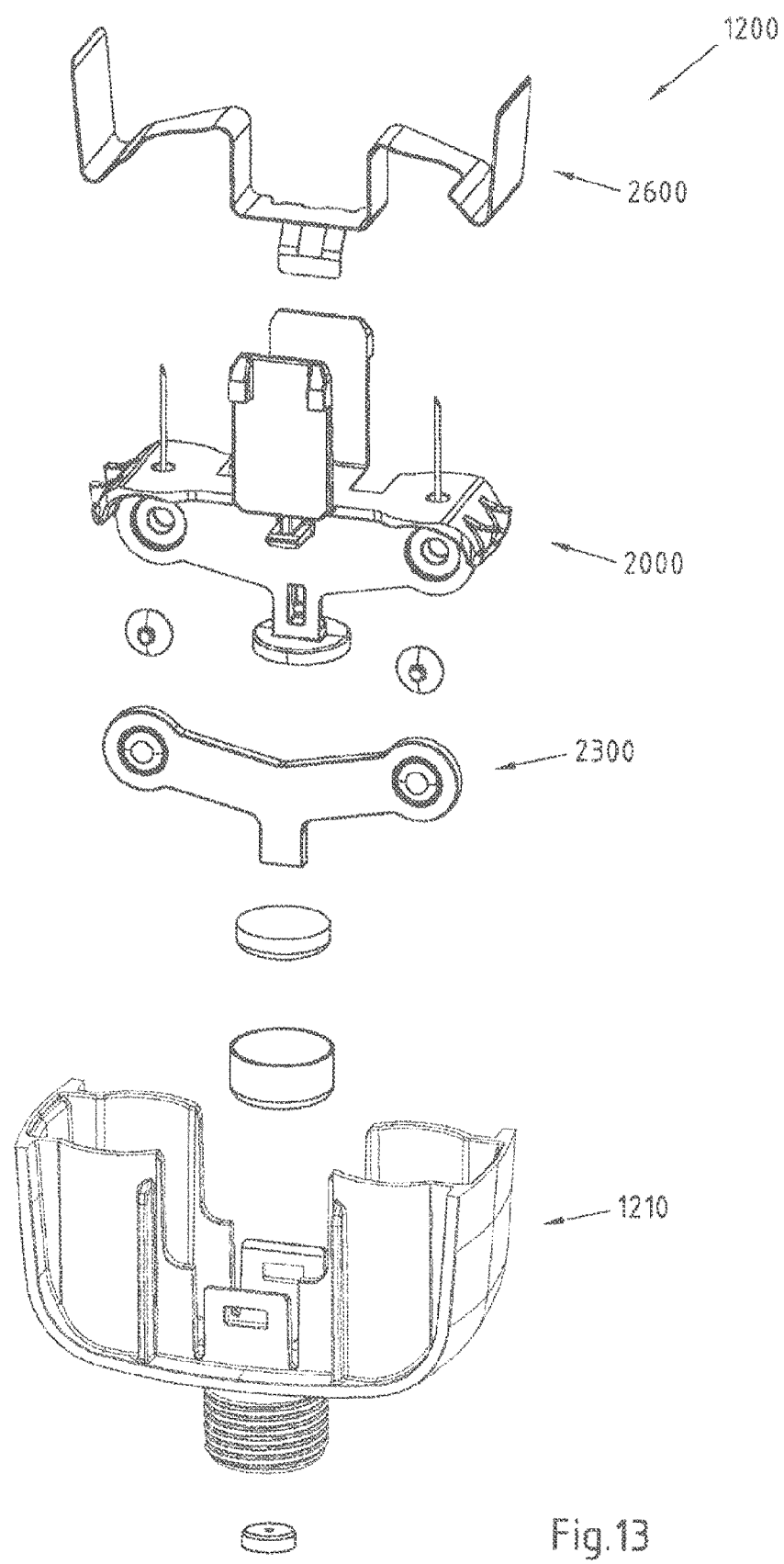
FIG. 13 illustrates an exploded view of the dispense interface illustrated in FIG. 12.

FIGS. 12 and 13 show a dispense interface 1200. As may be seen from FIG. 12 and the exploded view in FIG. 13, the dispense interface 1200 may comprise an outer body 1210 and in inner body 2000. The inner body 2000 may be seated within an interior space defined by the outer main body 1210. Preferably, it is the inner body 2000 of the dispense interface 1200 that is configured to be coupled to a distal end of a drug delivery device while also being securely positioned within an interior space defined by the outer body 1210. The dispense interface 1200 may further comprise a manifold 2300.

As may be further be seen from FIGS. 12 and 13 the dispense interface 2000 also comprises a lockout element in the form of a lockout spring 2600. One reason that a lockout element 2600 may be incorporated into a dispense interface 1200, is to ensure that once the dispense interface 1200 is removed from the drug delivery device, the dispense interface 1200 cannot be re-attached and used a second time. Preventing re-attachment tends to ensure that medicament is not allowed to reside in the dispense interface 1200 indefinitely and contaminate the drug delivered to the patient.

Figure 14:
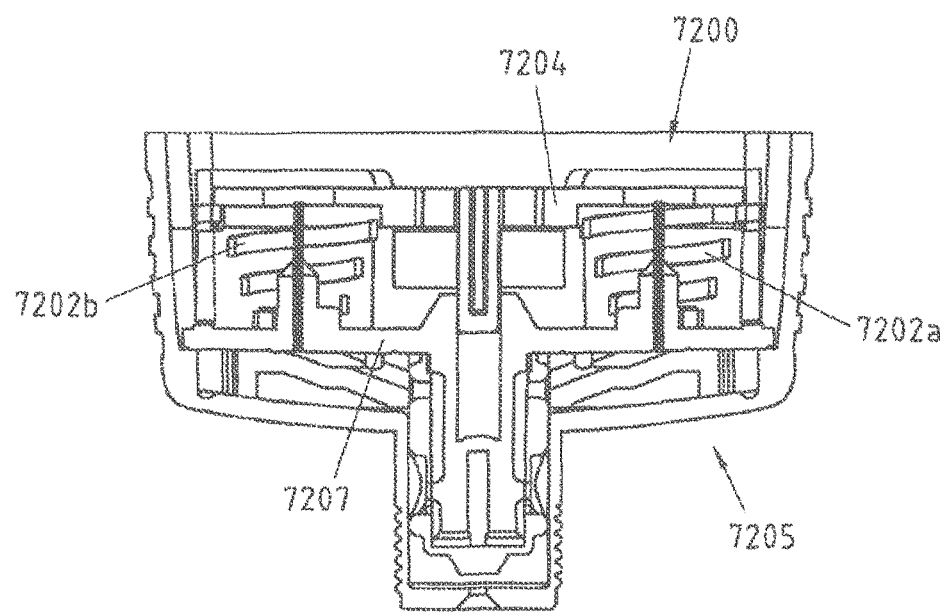
FIG. 14 illustrates a cross sectional view of an embodiment of the dispense interface according to the invention.

FIG. 14 illustrates a cross sectional view of an embodiment of the dispense interface 7205 according to the invention.

The dispense interface 7205 comprises an inner body 7207 and a lockout element 7200, which is coupled to the inner body 7207. In FIG. 14 the lockout element 7200 is in the receptive condition, in which the dispense interface is attachable to a drug delivery device. The lockout element 7200 comprises two spring elements 7202a and 7202b. Furthermore, the lockout element 7200 comprises a cover plate 7204 for bearing a distal portion of the drug delivery device, which cover plate 7204 is supported on the spring elements 7202a and 7202b.

Figure 15:
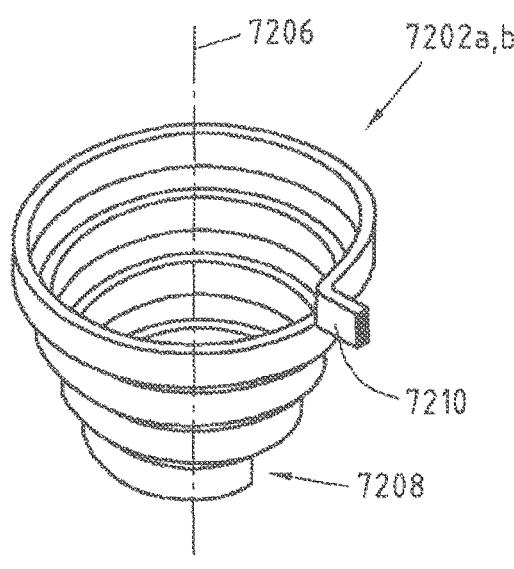
FIG. 15 illustrates a perspective view of a spring element in a receptive condition of the lockout element.
Figure 16:
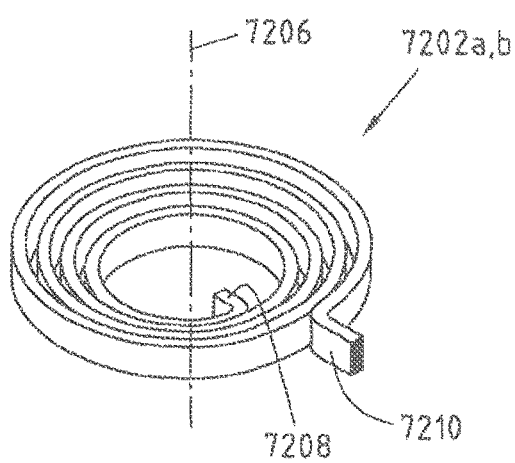
FIG. 16 illustrates a perspective view of a spring element in an activated condition of the lockout element.

FIG. 15 illustrates a perspective view of one such spring element 7202a,b in a receptive condition of the lockout element 7200 and FIG. 16 illustrates a perspective view of one such spring element 7202a,b in an activated condition of the lockout element 7200.

The spring element 7202a,b is a combined spiral and coil spring with a conical shape. The spring element 7202a,b has a spiral axis 7206 along which it may be compressed or around which it may be twisted.

By twisting the spring element 7202a,b around its axis 7206 it is strained in a first direction. By releasing the spring element 7202a,b around its axis 7206 it is relaxed in a second direction, which is opposite to the first direction.

By compressing the spring element 7202a,b along its axis 7206, it is strained in a third direction. By releasing the spring element 7202a,b along its axis 7206, it is relaxed in a fourth direction, which is opposite to the third direction.

Furthermore, the spring element 7202a,b has a first shaped element 7208 at its first end and a second shaped element 7210 at its second end.

Figure 17:
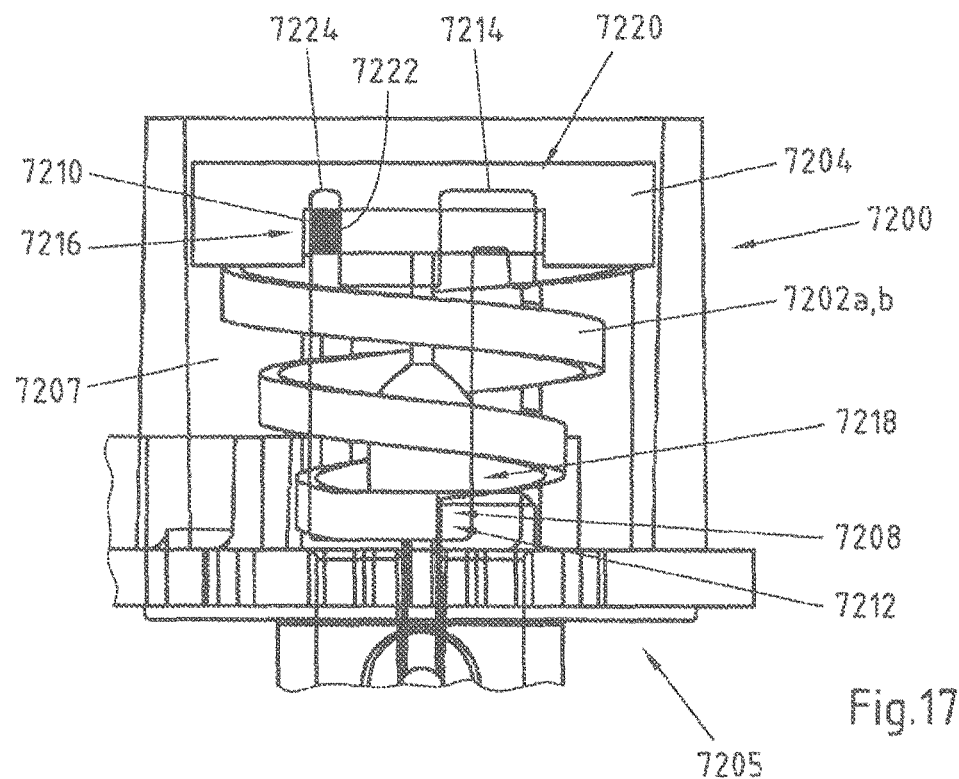
FIG. 17 illustrates a cross sectional view of a spring element seated onto the inner body of a dispense interface in a receptive condition of the lockout element.

FIG. 17 illustrates a cross sectional view of one such spring element 7202a,b seated onto the inner body 7207 of the dispense interface 7205 in a receptive condition of the lockout element 7200. As indicated, the first shaped element 7208 is seated with positive fit in a retaining element 7212 of the inner body 7207. At the same time the second shaped element 7210 is movably guided in a guiding track 7214 of the inner body 7207.

The guiding track 7214 has a receptive section 7216, an activation section 7218 and a blocking section 7220, wherein in the receptive condition the second shaped element 7210 is arranged in the receptive section 7216, wherein in the activated condition the second shaped element 7210 is arranged in the activation section 7218, and wherein in the locked condition the second shaped element 7210 is arranged in the blocking section 7220.

In the receptive condition of the lockout element 7200, as illustrated in FIG. 17 and already mentioned above, the second shaped element 7020 is positioned in the receptive section 7216 of the guiding track 7214. In this condition the spring element 7202a,b is strained in the first direction, and thus has a torsion strain imparted during assembly. Due to this torsion strain, the second shaped element is pressed by the spring force of the spring element 7202a,b in the second direction onto a first support portion 7222 of the guiding track 7214.

The spring element 7202a,b in this condition is at least partly relaxed in the fourth direction, thus at least partly relaxed along its spiral axis 7206, wherein preferably the spring element 7202a,b in this condition is not completely relaxed in the fourth direction, but strained in the third direction to some extent. This further causes the second shaped element 7210 to be pressed by the spring force of the spring element 7202a,b in the fourth direction onto a fourth support portion 7224 of the guiding track 7214.

Figure 18:
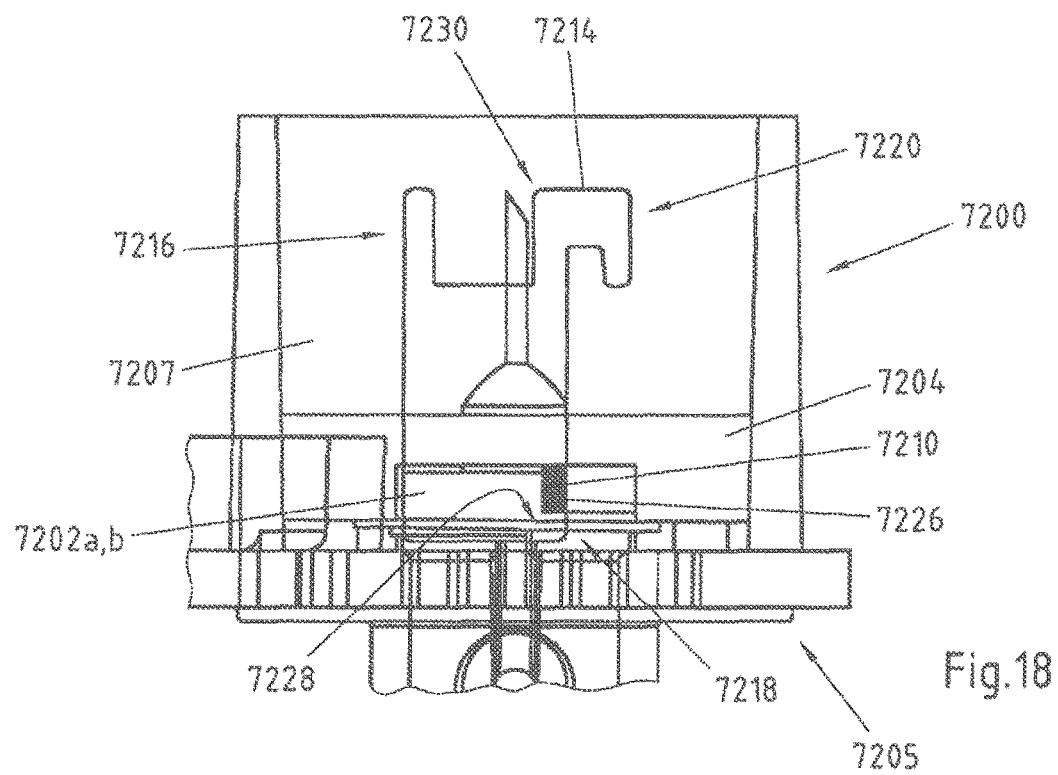
FIG. 18 illustrates a cross sectional view of a spring element seated onto the inner body of a dispense interface in an activated condition of the lockout element.

Upon fitting the dispense interface 7205 to a drug delivery device, the lockout element 7200 is moved from the receptive to the activated condition. Thereby a distal portion of the drug delivery device acts on the cover plate 7204, whereby the spring element 7202a,b is strained in the third direction and thus along its spiral axis. This causes the second shaped element 7210 to be moved from the receptive section 7216 into the activation section 7218, as illustrated in FIG. 18. Thereby the spring element 7202a,b is partly relaxed in the second direction, thus partly unwinds (or winds) around its axis 7206.

While positioned in the activation section 7218, the second shaped element 7210 is pressed by the spring force of the spring element 7202a,b in the second direction onto a second support portion 7226 of the guiding track 7214, since the spring element 7202a,b is not completely relaxed in the second direction. At the same time, the second shaped element 7210, while positioned in the activation section 7218, is pressed in the fourth direction against the cover plate 7204, due to the spring force applied by the spring element 7202a,b in the fourth direction.

Furthermore, while positioned in the activation section 7218, the second shaped element 7210 may be movable in the third and fourth direction between a distal stop position 7228, which is distant to the blocking section 7220, and a proximal stop position 7230, which is proximal to the blocking section 7220. Thereby, in the distal stop position 7228 the second shaped element 7210 is geometrically restricted from being further moved in the third direction, and in the proximal stop position 7230 the second shaped element 7210 may be geometrically restricted from being further moved in the fourth direction. In the proximal stop position 7230, the second shaped element 7210 is also geometrically restricted in the first direction.

Detaching the dispense interface 7205 from the drug delivery device causes the lockout element 7200 to move into the locked condition. Thereby the distal portion of the drug delivery device is retracted from the cover plate 7204, which causes the spring element 7202a,b to relax in the fourth direction, thus along the spiral axis 7206.

Therefore, the second shaped element 7210 is moved in the fourth direction along the activation section 7218 of the guiding track 7214. The second shaped element 7210 may be moved in the fourth direction up to the proximal stop position 7230, in which it is geometrically restricted from being moved further in the fourth direction.

In this proximal stop position 7230, the second shaped element 7210 is not any more supported in the second direction by the support portion 7226, thus the second shaped element 7210 is not any more restricted, but free to move in the second direction.

Figure 19:
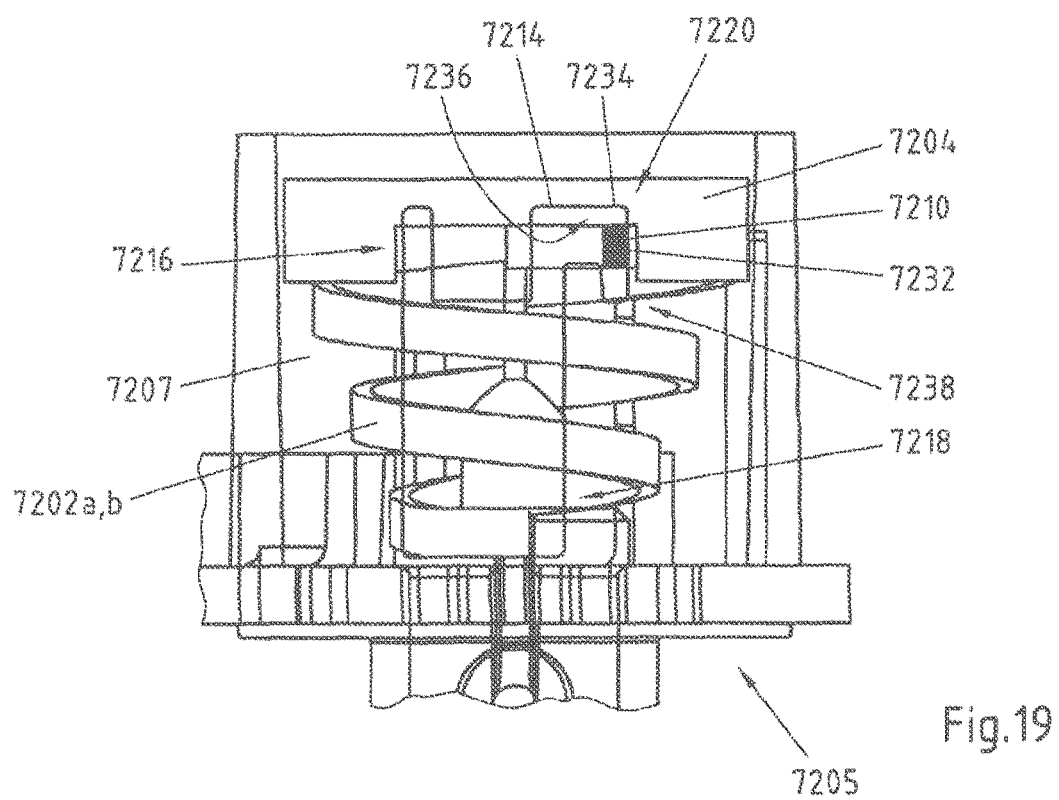
FIG. 19 illustrates a cross sectional view of a spring element seated onto the inner body of a dispense interface in a locked condition of the lockout element.

Since the spring element 7202a,b in the activated condition is still strained in the first direction and therefore provides a spring force for movement of the second shaped element 7210 into the second direction, the second shaped element 7210 moves automatically in the second direction into the blocking section 7220, as illustrated in FIG. 19.

In this locked condition of the lockout element 7200, in which the second shaped element 7210 is positioned in the blocking section 7220, the spring element 7202a,b is still strained up to a small extent in the first and the third direction. Thus the second shaped element 7210 is pressed by the spring force of the spring element 7202a,b in the second direction onto a third support portion 7232. At the same time the second shaped element 7210 is pressed by the spring force of the spring element 7202a,b in the fourth direction onto a fifth support portion 7234. Thus, the second shaped element 7210 is prevented from being moved back to the activation section 7218 or even the receptive section 7216.

Furthermore, in this locked condition of the lockout element 7200, in which the second shaped element 7210 is positioned in the blocking section 7220, the second shaped element 7210 is blocked in the third direction, thus the spring element 7202a,b may not be compressed along the spiral axis 7206 due to geometrical restrictions. However, the blocking of the second shaped element 7210 in the blocking section 7220 does not necessarily prevent any movement of the spring element 7202a,b. Rather, the second shaped element 7210, while arranged in the blocking section 7220, may be movable up to a comparably short distance in the third and fourth direction. Thereby, the second shaped element 7210, while positioned in the blocking section 7220, may be moved between a stop position 7236 in the fourth direction, in which the second shaped element is geometrically restricted from being further moved in the fourth direction, and a stop position 7238 in the third direction, in which the second shaped element may be geometrically restricted from being further moved in the third direction. These two stop positions 7236,7238 have thus a comparably short distance to each other, such that only movement of the second shaped element 7210 up to a short distance in the third and/or fourth direction is possible.

Accordingly, in the locked condition of the lockout element 7200, the spring element 7202a,b is prevented from being strained in the third direction, and thus compressed along its axis 7206, whereby also movement of the cover plate 7204 in the third direction is prevented. The cover plate 7204 may in this condition thus not approach the inner body 7207, whereby a reattachment of the dispense interface 7205 is prevented.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(w-carboxyheptadecanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-9),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group-Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. Dispense interface for use with a drug delivery device comprising
an inner body, and
a lockout element,
wherein the lockout element is coupled to the inner body,
wherein the lockout element is movable from a receptive condition to a locked condition,
wherein in the receptive condition the dispense interface is attachable to the drug delivery device,
wherein in the locked condition the dispense interface is not-attachable to the drug delivery device,
wherein the lockout element is configured to move from the receptive condition to the locked condition when said dispense interface is attached to and detached from said drug delivery device,
wherein the lockout element comprises at least a spring element, wherein the spring element is a combined spiral and coil spring, and wherein the spring element comprises a first shaped element at a first end and a second shaped element at a second end,
wherein the inner body comprises a retaining element, in which the first shaped element of the spring element is seated with positive fit,
wherein the inner body comprises a guiding track formed in the inner body and shaped to guide the second shaped element of the spring element through the guiding track both around a spiral axis of the spring element and along the spiral axis of the spring element, and
wherein the second shaped element of the spring element is seated in the guiding track and is movably guidable through the guiding track such that, when the lockout element moves from the receptive condition to the locked condition, the second shaped element is moved relative to the first shaped element through the guiding track both around the spiral axis and along the spiral axis.

2. Dispense interface according to claim 1, wherein the spring element is strained in a first direction in the receptive condition and is at least partly relaxed in a second direction in an activated and/or the locked condition, and wherein the second direction is opposite to the first direction.

3. Dispense interface according to claim 2, wherein the spring element is strained in a third direction in the activated condition and is at least partly relaxed in a fourth direction in the receptive and/or locked condition, and wherein the fourth direction is opposite to the third direction.

4. Dispense interface according to claim 3,
wherein the combined spiral and coil spring is strained in the first direction by moving its ends opposite to each other around a spiral axis, and
wherein the combined spiral and coil spring is strained in the third direction by compression along the spiral axis.

5. Dispense interface according to claim 2, wherein the spring element is partly relaxed in the second direction in the activated condition and is further relaxed in the second direction in the locked condition.

6. Dispense interface according to claim 1,
wherein the guiding track comprises geometrical restrictions defining a receptive section of the guiding track, geometrical restrictions defining an activation section of the guiding track, and geometrical restrictions defining a blocking section of the guiding track,
wherein the second shaped element is arranged in the receptive section in the receptive condition,
wherein the second shaped element is arranged in the activation section in the activated condition, and
wherein the second shaped element is arranged in the blocking section in the locked condition.

7. Dispense interface according to claim 6,
wherein the second shaped element, while arranged in the receptive section, is movable a first axial direction into the activation section,
wherein the second shaped element, while arranged in the activation section, is movable in a second axial direction into the blocking section, and
wherein the second shaped element, while arranged in the blocking section is blocked in the first axial direction.

8. Dispense interface according to claim 7, wherein the spring element and the guiding track are configured such that when said dispense interface is attached to said drug delivery device, a distal portion of the drug delivery device acts on the spring element, such that said spring element is strained in the first axial direction and the second shaped element is moved from the receptive section into the activation section, such that said spring element is partly relaxed in a radial direction.

9. Dispense interface according to claim 7, wherein the spring element and the guiding track are configured such that when said dispense interface is detached from said drug delivery device, a distal portion of the drug delivery device is retracted from said spring element such that said spring element is at least partly relaxed in the second axial direction and the second shaped element moves automatically from the activation section into the blocking section such that said spring element is further relaxed in a radial direction.

10. Dispense interface according to claim 6,
wherein the second shaped element, while arranged in the receptive section, is pressed in a radial direction against a first geometrical restriction of the guiding track by an elastic spring force applied by the spring element,
wherein the second shaped element, while arranged in the activation section, is pressed in the radial direction against a second geometrical restriction of the guiding track by an elastic spring force applied by the spring element,
wherein the second shaped element, while arranged in the blocking section, is pressed in the radial direction against a third geometrical restriction of the guiding track by an elastic spring force applied by the spring element,
wherein the third geometrical restriction is positioned relative to the second geometrical restriction in the radial direction, and
wherein the second geometrical restriction is positioned relative to the first geometrical restriction in the radial direction.

11. Dispense interface according to claim 1,
wherein the lockout element is movable from the receptive condition to an activated condition,
wherein in the activated condition the lockout element is configured to move to the locked condition when said dispense interface is detached from said drug delivery device, and wherein the lockout element is configured to move from the receptive condition to the activated condition when said dispense interface is attached to said drug delivery device.

12. Dispense interface according to claim 1, wherein the lockout element comprises a cover plate configured to bear a distal portion of the drug delivery device, which cover plate is supported on the spring element.

13. An apparatus comprising a dispense interface according to claim 1 and comprising a drug delivery device, wherein the dispense interface is removably attached to the drug delivery device.

\* \* \* \* \*